United States Patent
Thomas et al.

(10) Patent No.: US 6,569,828 B1
(45) Date of Patent: May 27, 2003

(54) CLEANING WIPE

(75) Inventors: Barbara Thomas, Princeton, NJ (US); Karen Wisniewski, Bound Brook, NJ (US); Philip Gorlin, Flemington, NJ (US); Josh Ghaim, Franklin Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/283,669

(22) Filed: Oct. 30, 2002

Related U.S. Application Data

(63) Continuation-in-part of application No. 10/086,165, filed on Feb. 27, 2002, now Pat. No. 6,432,904, which is a continuation-in-part of application No. 10/008,715, filed on Nov. 13, 2001, now Pat. No. 6,440,925.

(51) Int. Cl.$^7$ ................................................ C11D 17/00
(52) U.S. Cl. ...................... 510/438; 510/295; 510/424; 510/470; 510/473; 510/501; 510/503; 510/505; 510/506; 510/499; 134/42; 428/288; 15/209.1
(58) Field of Search .................................. 510/438, 295, 510/499, 424, 470, 473, 501, 503, 505, 506; 134/42; 428/288; 15/209.1

(56) References Cited

U.S. PATENT DOCUMENTS

| | | | | |
|---|---|---|---|---|
| 4,725,489 A | * | 2/1988 | Jones | 428/289 |
| 5,141,803 A | * | 8/1992 | Pregozen | 428/288 |
| 6,340,663 B1 | * | 1/2002 | Deleo et al. | 510/438 |
| 2002/0183233 A1 | * | 12/2002 | Mitra et al. | 510/438 |

* cited by examiner

*Primary Examiner*—Necholus Ogden
(74) *Attorney, Agent, or Firm*—Richard E. Nanfeldt

(57) ABSTRACT

The present invention relates to a cleaning wipe which is a water insoluble substrate impregnated with a cleaning composition containing a cellulosic polymer.

4 Claims, No Drawings

CLEANING WIPE

Related Application

This application is a continuation in part application of U.S. Ser. No. 10/086,165 filed Feb. 27, 2002 now U.S. Pat. No. 6,432,904 which in turn is a continuation in part application of U.S. Ser. No. 10/008,715 filed Nov. 13, 2001 now U.S. Pat. No. 6,440,925.

FIELD OF INVENTION

The present invention relates to a dishwashing cleaning wipe which is single or multi layer fabric substrate which has been impregnated with a liquid cleaning composition.

BACKGROUND OF THE INVENTION

The patent literature describes numerous wipes for both body cleaning and cleaning of hard surfaces but none describe wipes for cleaning dishware, flatware, pots and pans. U.S. Pat. Nos. 5,980,931, 6,063,397 and 6,074,655 teach a substantially dry disposable personal cleansing product useful for both cleansing and conditioning the skin and hair. U.S. Pat. No. 6,060,149 teaches a disposable wiping article having a substrate comprising multiple layers.

U.S. Pat. Nos. 5,756,612; 5,763,332; 5,908,707; 5,914,177; 5,980,922 and 6,168,852 teach cleaning compositions which are inverse emulsions.

U.S. Pat. Nos. 6,183,315 and 6,183,763 teach cleaning compositions containing a proton donating agent and having an acidic pH. U.S. Pat. Nos. 5,863,663; 5,952,043; 6,063,746 and 6,121,165 teaches cleaning compositions which are oil in water emulsions.

SUMMARY OF THE INVENTION

A single use cleaning wipe for dishwashing application comprises a water insoluble substrate, impregnated with a cleaning composition containing at least one surfactant, a cellulosic polymer and water.

The liquid cleaning compositions of this invention are not an emulsion and do not contain potassium sorbate, a polysaccharide polymer, a polycarboxylate polymer, polyvinyl alcohol polymer, polyvinylpyrrolidone polymer or methyl vinyl ether polymer.

DETAILED DESCRIPTION OF THE INVENTION

The present invention relates to a cleaning wipe for dishware, flatware, pots and pans which comprises approximately by weight:

(a) 5% to 80% of a cleaning composition which comprises approximately by weight:
  (i) 0.5% to 12% of a water soluble cellulosic polymer selected from the group consisting of methyl cellulose and hydroxypropyl methyl cellulose and mixtures thereof;
  (ii) 15% to 50% of at least one surfactant selected from the group consisting of alkali metal salts of a fatty acids, ethoxylated nonionic surfactants, amine oxide surfactants, alkyl polyglucoside surfactants, zwitterionic surfactants, anionic surfactants and $C_{12}$–$C_{14}$ fatty acid monoalkanol amides and mixtures thereof;
  (iii) 5 to 50%, more preferably 8% to 40% of at least one solubilizing agent;
  (iv) 0 to 0.5%, more preferably 0.05% to 0.25%, of an antibacterial agent;
  (v) 0 to 6%, more preferably 0.05% to 3% of a perfume; and
  (vi) the balance being water; and
(b) 20% to 95% of a water insoluble substrate, wherein said water insoluble substrate comprises a top layer of coarse fibers, an absorbent center layer which is cellulosic paper and a bottom layer of fine fibers, wherein the layers are bonded together and the center layer is impregnated with said cleaning composition.

The anionic surfactants which may be used in the detergent film of this invention are water soluble and include the sodium, potassium, ammonium and ethanolammonium salts of $C_8$–$C_{18}$ alkyl sulfates such as lauryl sulfate, myristyl sulfate and the like; linear $C_8$–$C_{16}$ alkyl benzene sulfonates; $C_{10}$–$C_{20}$ paraffin sulfonates; alpha olefin sulfonates containing about 10–24 carbon atoms; $C_8$–$C_{18}$ alkyl sulfoacetates; $C_8$–$C_{18}$ alkyl sulfosuccinate esters; $C_8$–$C_{18}$ acyl isethionates; and $C_8$–$C_{18}$ acyl taurates. Preferred anionic surfactants are the water soluble $C_{12}$–$C_{16}$ alkyl sulfates, the $C_{10}$–$C_{15}$ alkylbenzene sulfonates, the $C_{13}$–$C_{17}$ paraffin sulfonates and the alpha $C_{12}$–$C_{18}$ olefin sulfonates.

The higher alkyl mononuclear aromatic sulfonates, such as the higher alkylbenzene sulfonates containing 9 to 18 or preferably 9 to 16 carbon atoms in the higher alkyl group in a straight or branched chain. A preferred alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Preferred materials are set forth in U.S. Pat. No. 3,320,174, especially those in which the alkyls are of 10 to 13 carbon atoms.

Examples of suitable other sulfonated anionic detergents are the well known. The paraffin sulfonates may be mono-sulfonates or di-sulfonates and usually are mixtures thereof, obtained by sulfonating paraffins of 10 to 20 carbon atoms. Preferred paraffin sulfonates are those of $C_{12-18}$ carbon atoms chains, and more preferably they are of $C_{14-17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14-17}$ range will be minor and will be minimized, as will be any contents of di- or poly-sulfonates.

The $C_{8-18}$ ethoxylated alkyl ether sulfate surfactants have the structure

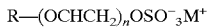

$$R-(OCHCH_2)_n OSO^-_3 M^+$$

wherein n is about 1 to about 22 more preferably 1 to 3 and R is an alkyl group having about 8 to about 18 carbon atoms, more preferably 12 to 15 and natural cuts, for example, $C_{12-14}$ or $C_{12-16}$ and M is an ammonium cation or a metal cation, most preferably sodium.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof, e.g., sodium myristyl (3 EO) sulfate.

Ethoxylated $C_{8-18}$ alkylphenyl ether sulfates containing from 2 to 6 moles of ethylene oxide in the molecule are also suitable for use in the invention compositions. These detergents can be prepared by reacting an alkyl phenol with 2 to 6 moles of ethylene oxide and sulfating and neutralizing the resultant ethoxylated alkylphenol.

The $C_{12}$–$C_{20}$ paraffin sulfonates may be monosulfonates or di-sulfonates and usually are mixtures thereof, obtained by sulfonating paraffins of 10 to 20 carbon atoms. Preferred paraffin sulfonates are those of $C_{12-18}$ carbon atoms chains, and more preferably they are of $C_{14-17}$ chains. Paraffin sulfonates that have the sulfonate group(s) distributed along the paraffin chain are described in U.S. Pat. Nos. 2,503,280; 2,507,088; 3,260,744 and 3,372,188 and also in German Patent 735,096. Such compounds may be made to specifications and desirably the content of paraffin sulfonates outside the $C_{14-17}$ range will be minor and will be minimized, as will be any contents of di- or poly-sulfonates.

The present invention can also contain alpha olefin sulfonates, including long-chain alkene sulfonates, long-chain hydroxyalkane sulfonates or mixtures of alkene sulfonates and hydroxyalkane sulfonates. These alpha olefin sulfonate surfactants may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred alpha olefin sulfonates contain from 14 to 16 carbon atoms in the R alkyl group and are obtained by sulfonating an a-olefin.

The long chain fatty acids are the higher aliphatic fatty acids having from about 8 to 22 carbon atoms, more preferably from about 10 to 20 carbon atoms, and especially preferably from about 12 to 18 carbon atoms, and especially preferably from 12 to 18 carbon atoms, inclusive of the carbon atom of the carboxyl group of the fatty acid. The aliphatic radical may be saturated or unsaturated and may be straight or branched. Straight chain saturated fatty acids are preferred. Mixtures of fatty acids may be used, such as those derived from natural sources, such as tallow fatty acid, coco fatty acid, soya fatty acid, mixtures of these acids, etc. Stearic acid and mixed fatty acids, e.g. stearic acid/palmitic acid, are preferred.

Thus, examples of the fatty acids include, for example, decanoic acid, dodecanoic acid, palmitic acid, myristic acid, stearic acid, behenic acid, oleic acid, eicosanoic acid, tallow fatty acid, coco fatty acid, soya fatty acid, mixtures of these acids, etc. Stearic acid and mixed fatty acids, e.g. stearic acid/palmitic acid, are preferred.

The nonionic surfactants which are used in the instant cleaning composition are selected from the group of an aliphatic ethoxylated nonionic surfactant and an aliphatic ethoxylated/propoxylated nonionic surfactant and mixtures thereof.

The water soluble aliphatic ethoxylated nonionic surfactants utilized in this invention are commercially well known and include the primary aliphatic alcohol ethoxylates and secondary aliphatic alcohol ethoxylates. The length of the polyethenoxy chain can be adjusted to achieve the desired balance between the hydrophobic and hydrophilic elements.

The nonionic surfactant class includes the condensation products of a higher alcohol (e.g., an alkanol containing about 8 to 16 carbon atoms in a straight or branched chain configuration) condensed with about 4 to 20 moles of ethylene oxide, for example, lauryl or myristyl alcohol condensed with about 16 moles of ethylene oxide (EO), tridecanol condensed with about 6 to 15 moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_9$–$C_{11}$ alkanol condensed with 4 to 10 moles of ethylene oxide (Neodol 91-8 or Neodol 91-5), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of about 8 to 15 and give good O/W emulsification, whereas ethoxamers with HLB values below 7 contain less than 4 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

One of the water soluble nonionic surfactants which can be utilized in this invention are an aliphatic ethoxylated/propoxylated nonionic surfactants which are depicted by the formula:

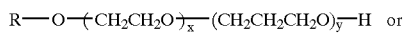
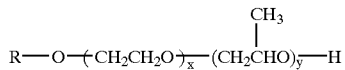

wherein R is a branched chain alkyl group having about 10 to about 16 carbon atoms, preferably an isotridecyl group and x and y are independently numbered from 1 to 20. A preferred ethoxylated/propoxylated nonionic surfactant is Plurafac® 300 manufactured by BASF.

The water-soluble zwitterionic surfactant, which can also be used provides good foaming properties and mildness. The zwitterionic surfactant is a water soluble betaine having the general formula:

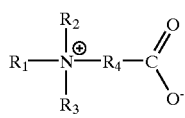

wherein $R_1$ is an alkyl group having 10 to 20 carbon atoms, preferably 12 to 16 carbon atoms, or the amido radical:

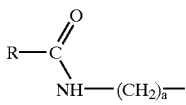

wherein R is an alkyl group having 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N,N-dimethyl-ammonia) acetate, coco dimethyl betaine or 2-(N-coco N, N-dimethylammonio) acetate, myristyl dimethyl betaine, palmityl dimethyl betaine, lauryl diemethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine.

Amine oxide semi-polar nonionic surfactants comprise compounds and mixtures of compounds having the formula:

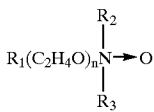

wherein $R_1$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_2$ and $R_3$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

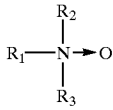

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 which is hereby incorporated herein by reference.

The alkyl polysaccharides surfactants, which can be used have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula

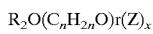

$R_2O(C_nH_{2n}O)r(Z)_x$ wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucosde content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, Pa. APG25 is a nonionic alkyl polyglycoside characterized by the formula:

$$C_nH_{2n+1}O(C_6H_{10}O_5)_xH$$

wherein n=10 (2%); n=122 (65%); n=14 (21–28%); n=16 (4–8%) and n=18 (0.5%) and x (degree of polymerization)= 1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35 C., 21 spindle, 5–10 RPM of 3,000 to 7,000 cps.

The cleaning composition can also contain a mixture of a $C_{12-14}$ alkyl monoalkanol amide such as lauryl monoalkanol amide and a $C_{12-14}$ alkyl dialkanol amide such as lauryl diethanol amide or coco diethanol amide.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc.

The cleaning composition can contain at least one solubilizing agent selected from the group consisting of a $C_{2-5}$ mono, dihydroxy or polyhydroxy alkanols such as ethanol, isopropanol, glycerol ethylene glycol, diethylene glycol, propylene glycol, and hexylene glycol and mixtures thereof, urea, and alkali metal cumene or xylene sulfonates such as sodium cumene sulfonate and sodium xylene sulfonate.

The cleaning composition of this invention may, if desired, also contain other components either to provide additional effect or to make the product more attractive to the consumer. The following are mentioned by way of example: Colors or dyes in amounts up to 0.5% by weight; pH adjusting agents, such as sulfuric acid or sodium hydroxide, can be used as needed.

Preservatives which can be used in the instant compositions at a concentration of 0.005 wt. % to 3 wt. %, more preferably 0.01 wt. % to 2.5 wt. % are: benzalkonium chloride; benzethonium chloride,5-bromo-5-nitro-1,3dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N'-(hydroxy methyl) urea; 1-3-dimethyol-5,5-dimethyl hydantoin; formaldehyde; iodopropynl butyl carbamata, butyl paraben; ethyl paraben; methyl paraben; propyl paraben, mixture of methyl isothiazolinone/methyl-chloroisothiazoline in a 1:3 wt. ratio; mixture of phenoxythanol/butyl paraben/methyl paraben/propylparaben; 2-phenoxyethanol; trishydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triazaazoniaadamantane chloride; and sodium benzoate. PH adjusting agents such as sulfuric acid or sodium hydroxide can be used as needed.

The cellulosic polymer which is used in the cleaning composition is selected from the group consisting of methyl cellulose and hydroxy propyl methyl cellulose Dow Chemical manufactures these cellulosic polymers under the tradename Methocel. The following chart set forth suitable Methocel polymer useful in the instant invention.

| | Methoxyl degree of substitution | Methoxyl (%) | Hydroxypropyl degree of substitution | Hydroxypropyl (%) |
|---|---|---|---|---|
| Methocel A | 1.8 | 30 | — | — |
| Methocel E | 1.9 | 29 | 0.23 | 8.5 |
| Methocel F | 1.8 | 28 | 0.13 | 5.0 |
| Methocel J | 1.3 | 18 | 0.82 | 27 |
| Methocel K | 1.4 | 22 | 0.21 | 8.1 |
| Methocel 310 Series | 2.0 | 25 | 0.8 | 25 |

The cellulosic polymer acts to regulate and slow the release of the cleaning composition from the water insoluble substrate.

The cleaning composition is made by preparing aqueous surfactant solution and a aqueous polymeric solution of the cellulosic polymer at a 12 wt. % to 18 wt. % of the cellulosic polymer. The surfactant composition solution and the polymeric solution are mixed by simple mixing at room temperature in a 4:1 to 1:4 weight ratio to form the cleaning solution which is to impregnate the water insoluble substrate.

The bottom and top layers may have different textures and abrasiveness. Differing textures can result from the use of different combinations of materials or from the use of different manufacturing processes or a combination thereof. A dual texture substrate can be made to provide the advantage of a more abrasive side for cleaning difficult to remove soils. A softer side can be used for more delicate or less soiled surfaces. The substrate should not dissolve or break apart in water. It is the vehicle for delivering the cleaning composition to dishware, flatware, pots and pans. Use of the substrate enhances lathering, cleaning and grease removal.

A wide variety of materials can be used as the substrate. It should have sufficient wet strength, abrasivity, loft and porosity. Examples include, non woven substrates, wovens substrates, hydroentangled substrates and sponges.

Examples of suitable non woven water insoluable substrates include, 100% cellulose Wadding Grade 1804 from Little Rapids Corporation, 100% polypropylene needlepunch material NB 701-2.8—W/R from American Nonwovens Corporation, a blend of cellulosic and synthetic fibres-Hydraspun 8579 from Ahlstrom Fibre Composites, and &0% Viscose/30% PES Code 9881 from PGI Nonwovens Polymer Corp.

Another useful substrate is manufactured by Jacob HolmLidro Rough'n Soft. It is a composition material comprising a 65/35 viscose rayon/polyester hydroentangled spunlace layer with a hydroenlongated bonded polyeser scribbly layer.

Still another useful substrate is manufactured by Texel. It is a composite material manufactured from a top layer of coarse fiber 100% polypropylene needlepunch, a center layer of an absorbent cellulose core and a bottom layer of a fine fiber polyester layer needlepunched together. The polypropylene layer can range from 1.5 to 3.5 oz./sq. yd. The cellulose core is a didn't we hear that the use of the word "crepe" brings problems—or is that just saying "crepe paper" and not "creped paper"? paper layer ranging from 0.5 to 2 oz./sq. yd. The fine fiber polyester layer can range from 0.5 to 2 oz./sq. yd. At least 50 wt. % of the impregnated cleaning composition is contained within the cleaning cellulose core layer.

The product of the present invention comprising mutliple layers may be ultrasonically bonded with appropriate choice of materials after applying the coating of one or more of the layers. Alternatively layers may be bonded together by needlepunch, mechanical means such as sewing, thermal bonding, chemical bonding, or sonic bonding prior to impregnation.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following cleaning composition (in wt. %) was prepared by simple batch mixing at room temperature. Then, cellulosic core layer was impregnated with the cleaning composition at a rate of 15.9 grams per 100 square inches of cellulose core. The cellulose core is Wadding Grade 1804 made by Little Rapids Corporation. The impregnated cellulosic core was sandwiched between a coarse fiber 100% polypropylene layer and a fine fiber polyester layer. The three layers were joined together by sewing.

|  | A |
|---|---|
| Part I |  |
| Ethanol | 33.0 |
| Sodium linear alkyl benzene sulfonate | 23.6 |
| Methyl cellulosic polymer | 1.4 |
| Water | Bal. |
| Part 1 Formula A | 1 |
| Three layer composite substrate | 1 |

While particular embodiments of the invention and the best mode contemplated by the inventors for carrying out the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

What is claimed:

1. A cleaning wipe which comprises approximately by weight:
   (a) 20% to 95% of a water insoluble substrate which comprises a top layer of coarse fibers, an absorbent center layer, and a bottom layer of fine fibers, wherein the three layers are bonded together; and
   (b) 5% to 80% of a cleaning composition which comprises approximately by weight:
      (i) 0.5% to 12% of a water soluble cellulosic polymer selected from the group consisting of methyl cellulose and hydroxypropyl methyl cellulose and mixtures thereof; and
      (ii) 15% to 50% of at least one surfactant selected from the group consisting of alkali metal salts of a fatty acid ethoxylated nonionic surfactants, amine oxide surfactants, alkyl polyglucoside surfactants, zwitterionic surfactants, anionic surfactants and $C_{12}$–$C_{14}$ fatty acid monoalkanol amides and mixtures thereof;
      (iii) 5% to 50% of at least one solubilizing agent;
      (iv) 0.005% to 3% of a preservative selected from the group consisting of N-(hydroxymethyl)-N-(1,3-dihydroxy methyl-2,5-dioxo-4-imidaxolidinyl-N-(hydroxyl methyl)urea and iodopropynyl butyl carbamata; and
      (v) the balance being water, wherein only the center absorbent layer is impregnated with said cleaning composition and wherein said cleaning composition is not an emulsion and does not contain potassium sorbate, a polycarboxylate polymer, polyvinyl alcohol polymer, polyvinylpyrrolidone polymer or methyl vinyl ether polymer.

2. A wipe according to claim 1 wherein said cleaning composition further includes 0.1 wt. % to 0. 5 wt. % of an antibacterial agent.

3. A wipe according to claim 1 wherein said solubilizing agent is a $C_2$–$C_5$ alkanol.

4. A wipe according to claim 1 wherein said cleaning composition further includes 0.1 wt. % to 1.5 wt. % of a perfume, essential oil or a water insoluble organic compound.

* * * * *